United States Patent
Hennion

(10) Patent No.: US 6,847,852 B2
(45) Date of Patent: Jan. 25, 2005

(54) FORCE FEEDBACK MEMBER CONTROL METHOD AND SYSTEM

(75) Inventor: Bernard Hennion, St. Martin d'Uriage (FR)

(73) Assignee: France Télécom, Paris (FR)

( * ) Notice: Subject to any disclaimer, the term of this patent is extended or adjusted under 35 U.S.C. 154(b) by 220 days.

(21) Appl. No.: 09/992,583

(22) Filed: Nov. 14, 2001

(65) Prior Publication Data

US 2002/0082724 A1 Jun. 27, 2002

(30) Foreign Application Priority Data

Nov. 15, 2000 (FR) .......................................... 00 14733

(51) Int. Cl.[7] .............................................. G05B 13/02
(52) U.S. Cl. ............................. 700/45; 700/44; 700/37; 700/65; 700/66; 709/203; 709/204; 709/217; 709/219
(58) Field of Search ............................. 700/28, 29, 30, 700/31, 45, 46, 65, 66, 44, 37; 709/217–218, 219, 203, 204

(56) References Cited

U.S. PATENT DOCUMENTS

| | | | | |
|---|---|---|---|---|
| 4,925,312 A | * | 5/1990 | Onaga et al. ................ 700/261 |
| 5,629,594 A | * | 5/1997 | Jacobus et al. ......... 318/568.11 |
| 5,659,480 A | * | 8/1997 | Anderson et al. ........... 700/186 |
| 5,754,023 A | * | 5/1998 | Roston et al. ............... 318/561 |
| 5,904,724 A | * | 5/1999 | Margolin ..................... 701/120 |
| 5,912,454 A | * | 6/1999 | Castillo et al. .............. 250/205 |
| 6,219,589 B1 | * | 4/2001 | Faraz et al. ................. 700/254 |
| 6,366,272 B1 | * | 4/2002 | Rosenberg et al. .......... 345/156 |

FOREIGN PATENT DOCUMENTS

| | | |
|---|---|---|
| FR | 2 646 612 | 11/1990 |
| WO | WO 98/06024 | 2/1998 |

OTHER PUBLICATIONS

"A Remote Collaboration System Using Hand–Force Virtual Environment"; Makoto Sato, Masahiro Ishii, Yasuhide Yamamoto, Ryo Tkamatsu, and Hiroshi Kawarada; Electronics and Communications in Japan, Part 3, vol. 80 No. 4, 1997 translated from Denshi Joho Tsushin Gakkai Ronbunshi, vol. 79–A, No. 2, 1996, pp. 481–488.

International Search Report; EPO Form 1503 12.99 (P04C14); Jul. 7, 2001.

* cited by examiner

*Primary Examiner*—Ramesh Patel
(74) *Attorney, Agent, or Firm*—Meyertons, Hood, Kivlin, Kowert & Goetzel, P.C.; Eric B. Meyertons

(57) ABSTRACT

A method and a system for controlling a force feedback member able to interact with another member, including a local model for calculating a set point addressed to the force feedback member from a plurality of variables, and a remote model for estimating interactions and variables of the other member, with updating on receiving data from another remote system, and resynchronizer means able to send a resynchronization message to the other system.

11 Claims, 4 Drawing Sheets

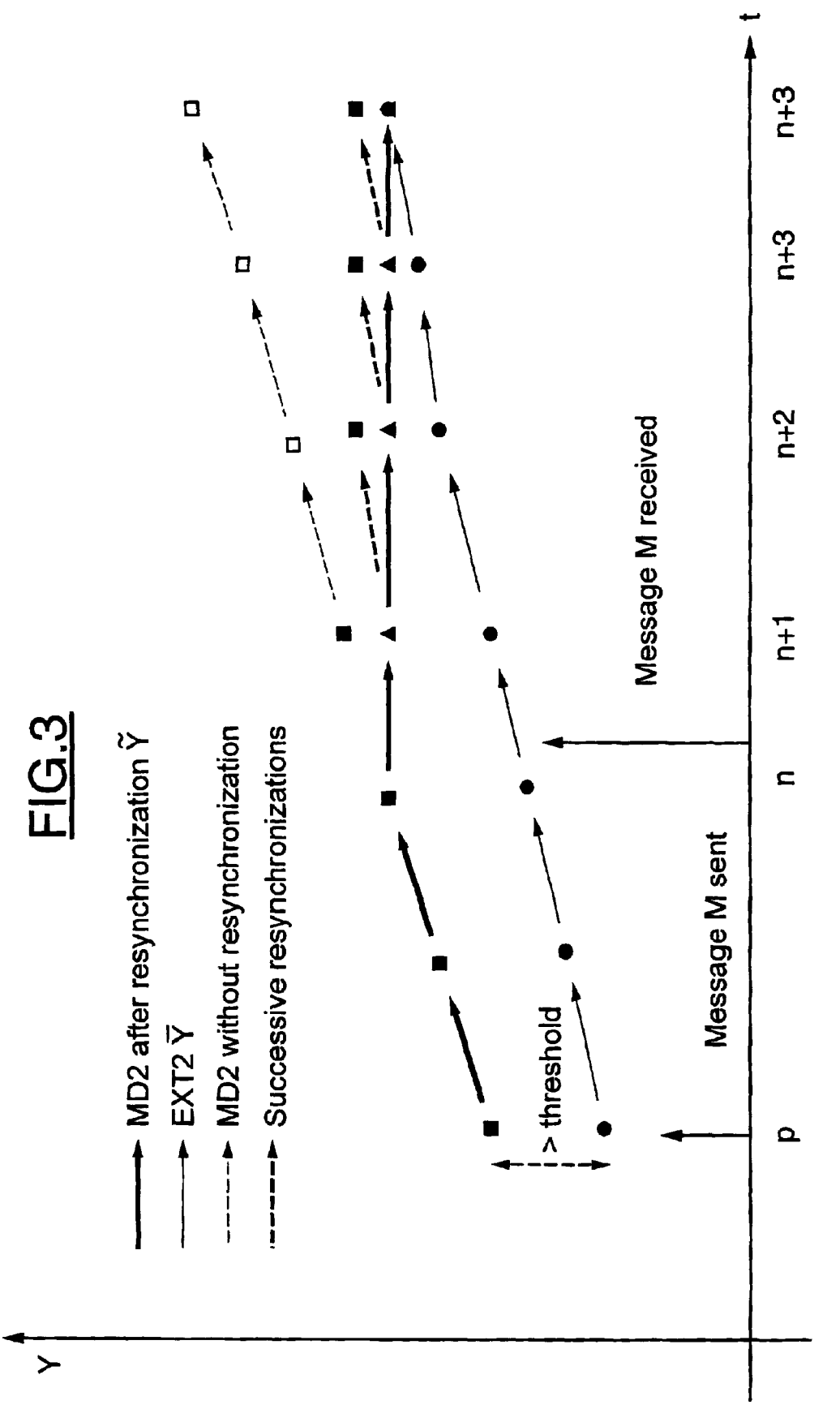

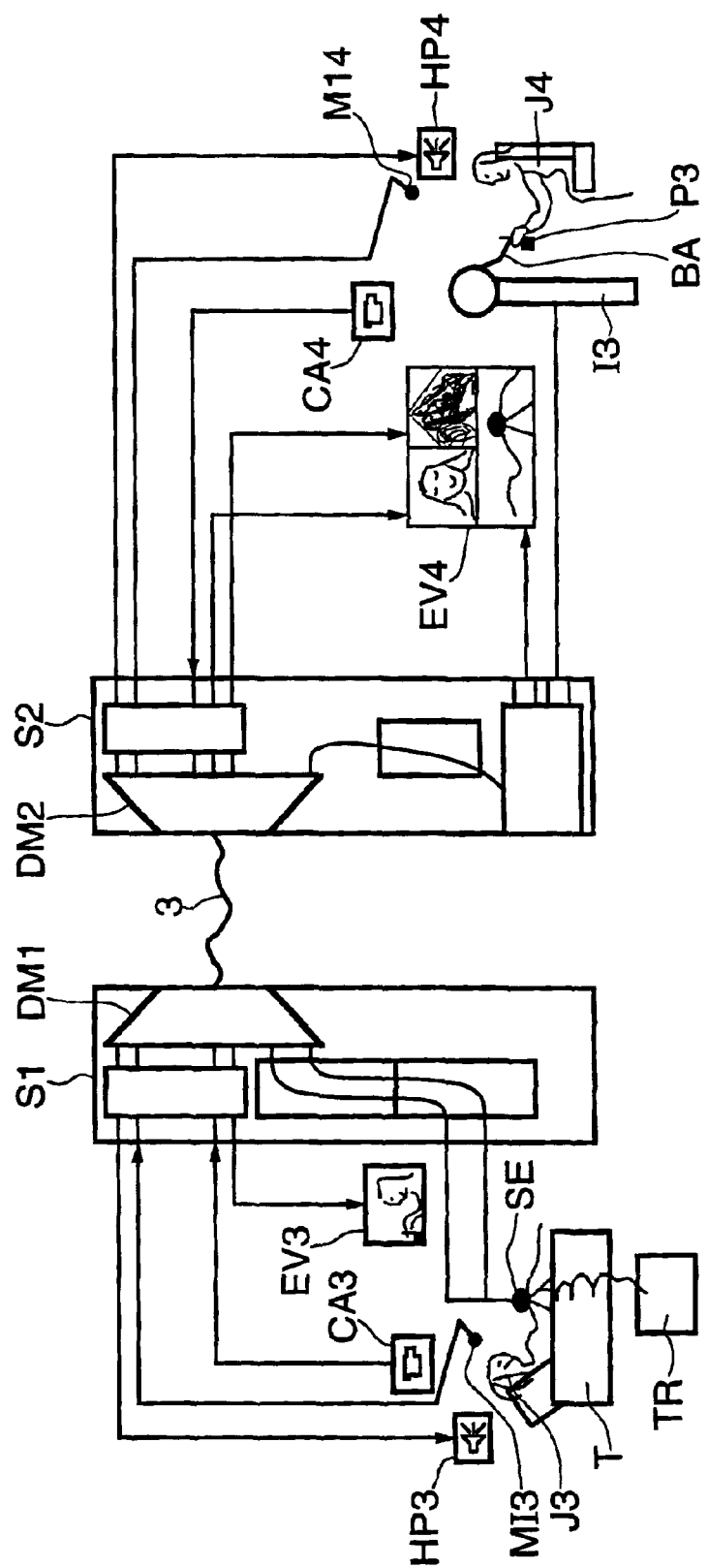

FORCE FEEDBACK MEMBER CONTROL METHOD AND SYSTEM

BACKGROUND OF THE INVENTION

1. Field of the Invention

The present invention relates to transmission of force feedback over a long distance, in particular in the context of developing distributed virtual worlds and telepresence systems.

2. Description of the Prior Art

In the same way that digital video coding techniques are based on a knowledge of visual perception and voice recognition techniques are based on a knowledge of hearing, haptic techniques (from the Greek haptos: hand) are based on a knowledge of gestures.

There are two sorts of fine gesture that can be executed by the hand: ballistic gestures, such as moving the hand toward a glass before taking hold of it, and gestures with touch feedback, such as moving the glass toward the mouth after taking hold of it and closing the clamp formed by the thumb and the fingers. The brain is then informed continuously of the force with which the hand is gripping the glass and of the weight of the glass, which depends on the quantity of liquid in it. The brain then reacts by giving the motor instruction to "grasp" the glass sufficiently tightly for it not to be dropped, but not too tightly, so as not to break it or expend energy uselessly.

Ballistic gestures activate the motor reflex arc but they do not activate the touch feedback sensing reflex arc. Force feedback can be a visual representation of the space, but also a gestural map, that is to say a learned or innate mental representation hardwired into the brain and which automatically generates the sequence of motor instructions to the muscles of the shoulder, the arm and the hand to perform the ballistic gesture as a function of a particular mental representation of the space, in particular of the assumed hand-glass distance.

For ballistic gestures, it is sufficient to transmit information on the gesture to the brain with a sampling frequency of 100 Hz. This means that if a sample of the signal is sent every 10 ms, the signal transmitted will contain all the information pertinent to the ballistic gesture.

Gestures with touch feedback simultaneously activate the motor reflex arc and the sensing reflex arc. The brain closes the loop and in humans the complete cycle takes less than 1 ms. The bandwidth of the sensing neurons in the ends of the fingers, i.e. the maximum mechanical signal frequency that the neurons can detect and transmit to the brain, is greater than 500 Hz. To be able to code a fine gesture in a computer, the force feedback system used must itself have a high operating frequency, in accordance with Shannon's theorem a frequency of at least twice the bandwidth of the fingers.

In practice, force feedback systems on a local machine typically operate at a frequency of 1 kHz and in a local closed loop, meaning that feedback is calculated and then applied to their motors and then perceived by the hand every $\frac{1}{1000}$ second. This avoids the effect known as the "electric toothbrush" effect: the instrument held in the hand must not give the impression of vibrating.

The frequency of 1 kHz results from the following compromise: it must not be too low, if the tactile impression is to be reproduced finely, or too high, if the computer is to have sufficient time to calculate the feedback force that will represent the fine simulation of the gesture executed in the virtual mechanical world.

If it is necessary to transmit via a telecommunication network fine gestures coded by the force feedback system and fine gestures with feedback, the problem is more complicated because of the generally much greater latency introduced by the network itself.

Using the ISDN technology, the latency is 30 ms, using the ADSL technology it is of the order of 200 ms, and on the Internet it can be as much as 6 s or even lead to the message being purely and simply rejected. The ADSL and Internet latency varies because of the asynchronous nature of the networks. The frequency of 1 kHz is therefore much too high to be maintained if the closed loop includes a return trip via the network—the gesture is coded and then transmitted via the network, applied to a remote object, and feedback from the object is in turn coded and sent back via the network.

A ballistic gesture can be transmitted with a time-delay of the order of 10 ms. Sight is a monodirectional sense: the eye is a kind of camera recording a scene and, ignoring a tolerance value, the brain can perceive the precise visual film with a slight time-delay without disturbing the execution of the gesture.

On the other hand, a fine gesture with feedback requires a loop of less than one millisecond for the return trip to make the decision on the intensity of the force to be applied:

sending of the instruction to the muscle via the motor sensing reflex arc, mechanical action of the hand on the glass, sensation at the ends of the fingers of touching the glass (increased contact pressure), and return of information to the brain via the tactile sensing reflex arc to enable the brain to decide to adjust the force applied to the "clamp".

A method known as the "wave transform" method for transmitting this kind of fine gesture is nevertheless described by John Wilson and Neville Hogan of MIT in "Algorithms for Network-Based Force Feedback", Fourth PHANTOM Users Group Workshop (PUG 99). The method simulates the time-delay introduced by the network by means of an artificial viscosity that stabilizes the feedback loop: the greater the time-delay introduced by the network, the more viscous the system.

The "wave transform" method transposes into the force/speed space the theory of passive quadripole networks with pure time-delay that is well known to the skilled person for electrical voltage/current parameters. The theory is used to calculate the incident and reflected electrical waves as a function of the characteristic impedance of the line. Transmission of the electrical signal is optimized if the line is terminated with the same characteristic impedance.

Ohm's law $U=Z \times I$ is transposed into the mechanical space by the law $F=Viscosity \times Speed$ and the "wave transform" method consists of adapting a virtual pure time-delay line by assigning it a characteristic impedance (in reality a viscosity), which is that of the remote-controlled robot. The signal is transmitted in the form of its Z transform, $S(z)=\Sigma (s(t) \times e^{(2i \times \pi \times n \times T)})$ in which T is the fixed time-delay of the network. The greater the time-delay introduced by the network, the greater the artificial viscosity that must be introduced into the line to stabilize the distributed mechanical simulation of the fine gesture in a closed loop in the network.

The gestural sensation is undoubtedly distorted, but transmission of the useful signal is optimized. This method was published following the Fourth Users Group Workshop (PUG99).

The "wave transform" method requires a synchronous network, i.e. a network whose time-delay is fixed and known, for example an ISDN. It is based on the Z representation of sampled discrete signals whose period is equal to the known fixed time-delay of the network.

It is therefore inapplicable to message-based asynchronous Internet, ATM or UMTS type networks, which are characterized by a variable transmission time-delay and by a rejection if the message is lost or takes too long to cross the network.

The problem of the excessively fast timing of force feedback systems is exacerbated in asynchronous networks, for which:

messages can be lost or rejected or fail to arrive if the acknowledgement is delayed for too long (TCP/IP), messages which reach the correct destination take a variable time to cross the network, they do not necessarily arrive in the order in which they were sent, and there is no common clock for the two machines accurate to within one millisecond.

The invention proposes to remedy the drawbacks of the prior art systems.

SUMMARY OF THE INVENTION

The invention proposes a control system for a force feedback member able to interact with another member, of the type with a time constant less than that associated with remote control, which system includes a local model for calculating a set point addressed to the force feedback member from a variable measured by the force feedback member, variables intrinsic to the force feedback member, an estimate of an external interaction with the force feedback member, and a state variable of the force feedback member, a remote model for estimating interactions and state variables of the other member with updating on receipt of data from another remote system, and resynchronizer means able to send a resynchronization message to the other system.

Thus the behavior of the remote element is simulated locally.

The system advantageously includes a phantom model for obtaining an estimate of state variables of the force feedback member and resynchronizing the estimate on reception of the resynchronization message. The phantom model is used to simulate locally the remote model of the remote control system.

In one embodiment of the invention, the resynchronizer means include comparator means for comparing the estimate of state variables from the phantom model and state variables from the local model so that in the event of a difference exceeding a predetermined threshold the resynchronization means can send a resynchronization message to the phantom model and to the other system.

In one embodiment of the invention, the system includes extrapolator means for processing a resynchronization message for updating the remote model received from the other system.

The invention also proposes a system for controlling two force feedback members situated at a distance from each other. Each member is provided with a control system including a local model for calculating a set point addressed to the force feedback member from a variable measured by the force feedback member, variables intrinsic to the force feedback member, an estimate of an external interaction with the force feedback member, and a force feedback member status variable, a remote model for estimating interactions and state variables of the other member, with updating on reception of data received from another, remote system, and resynchronization means adapted to send a resynchronization message to the other system.

The invention also proposes a method of controlling a force feedback member able to interact with another member, the method including:

local modeling to obtain a set point sent to the force feedback member from a variable measured by the force feedback member, variables intrinsic to the force feedback member, an estimate of an external interaction with the force feedback member, and a state variable of the force feedback member;

remote modeling of the interactions and the state variables of the other member with updating on receiving data from another remote system;

generating a resynchronization message and sending it to said other system.

The method advantageously includes phantom modeling of state variables of the force feedback member with resynchronization on receiving the resynchronization message.

In one embodiment of the invention, at the time of resynchronization, the estimate of state variables from the phantom modeling and state variables from the local modeling are compared so that in the event of a difference exceeding a predetermined threshold a resynchronization message can be sent to the other system with a view to new phantom modeling.

One embodiment of the invention includes extrapolation to process a resynchronization message from the other system and to update the remote modeling.

The invention also provides a computer program including program code means for executing the steps of the method when said program runs on a computer.

The invention also provides a medium capable of being read by a reader and storing program code means for executing the steps of the method when said program runs on a computer.

The present invention applies with advantage to bidirectional systems, for example video games with control handgrips provided with force feedback actuators, and to robotized remote ultrasound scanning, which can be used in the field of obstetrics and for abdominal examinations.

In the case of ultrasound scanning, the skin of the patient is generally coated with a gel to ensure correct transmission of the ultrasound. The ultrasound probe can be manipulated at a distance by an operator. Because of the presence of the gel, the components of force exerted by the patient on the probe can be considered as normal to the local surface of the skin. The probe has six degrees of freedom with force feedback with respect to three axes of a three-dimensional system of axes and torque feedback, also with respect to the three axes of a three-dimensional system of axes. The system can also apply to remote combat games, fencing games or industrial applications of the telemachining type.

The present invention will be better understood and other advantages will become apparent on reading the following detailed description of a few embodiments, which description is given by way of non-limiting example only and illustrated by the accompanying drawings.

BRIEF DESCRIPTION OF THE DRAWINGS

FIG. 3 shows evolution curves for some parameters of the system.

FIG. 4 is a diagrammatic view of a second embodiment of the invention.

DETAILED DESCRIPTION OF THE PREFERRED EMBODIMENTS

Figure 1:
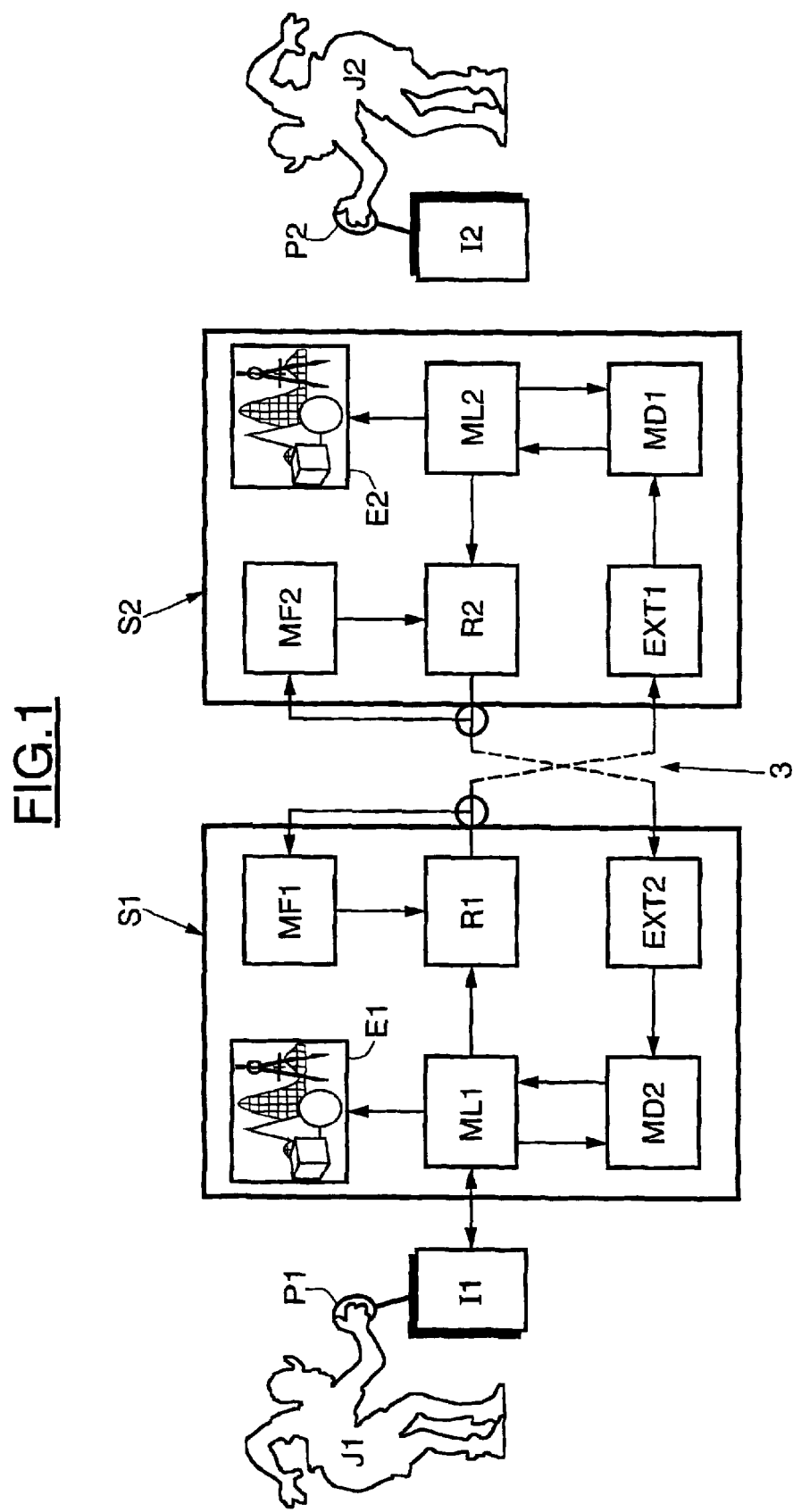
FIG. 1 is a diagrammatic view of a first embodiment of a system according to the invention.

As can be seen in FIG. 1, a game system in which players J1 and J2 compare their strength remotely—this kind of game is often referred to as an "iron arm" game—includes a handgrip P1 for the player J1 and a handgrip P2 for the player J2. Each handgrip P1, P2 is connected to an interface I1, I2 including means for exerting a force on the handgrip P1, P2, for example an electric actuator, and means for measuring the force exerted by the player J1, J2 on the handgrip P1, P2, for example a torque sensor or a strain gauge. The interface I1, I2 also includes an acquisition card connected to the means for exercising a force and to the measuring means and able to exchange digital data with another digital system such as a computer.

Each interface I1, I2 is connected to a control system S1, S2. In the case shown here, the systems S1 and S2 are identical. Only the system S1 is described. However, embodiments in which one of the two systems is of simplified structure compared to the other one can be envisaged.

Generally speaking, the system S1 can take the form of a personal computer, generally provided with at least one microprocessor, random access memory and read-only memory, a communication bus, input and output ports and one or more programs stored in memory and executed by the microprocessor.

The system S1 is connected on the one hand to the interface I1, for example by an RS 232 bus, and to the system S2 by a communication network 3, which can be a synchronous network (for example an ISDN) or an asynchronous network (for example an ATM or UMTS network or a TCP/IP network like the Internet). The system S1 is located near the player J1, for example in the same room. The system S2 is at a distance from the system S1 from a few meters to a few thousand kilometers. In other words, the system S1, the interface I1, the handgrip P1 and the player J1 can be described as "local" and the system S2, the interface I2, the handgrip P2 and the player J2 can be described as "remote".

To be more precise, the system S1 includes a local model ML1 able to send the interface I1 a set point $F_e$ and to receive from said interface I1 a variable measured by the interface I1, for example the position X of the handgrip P1. The set point can be a force or torque variable. The system S1 includes a remote model MD2 adapted to estimate a state of the local model ML2 of the system S2. The remote model MD2 of the system S1 can receive data from the system S2 and from the local model ML1 and can send data to the local model ML1. To be more precise, the system S1 includes an extrapolator EXT2 receiving data from the system S2 via the communication network 3 in order to process a resynchronization message from the system S2 and transmit update data to the remote model MD2 as a function of the resynchronization message received last.

The system S1 includes a screen E1 connected to the local model ML1 to display data from the local model ML1, for example a curve tracing the evolution of the forces exerted on and the positions of the handgrips P1 and P2.

The system S1 includes a resynchronizer R1 receiving data from the local model ML1 and adapted to send output data to the system S2, in particular to the extrapolator EXT1 of the system S2. The resynchronizer R1 can handle data preparation for sending the data in the form of a resynchronization message that can include a time/date, the position X of the handgrip P1, the force F exerted on the handgrip P1 at said time/date and the force exerted on the handgrip P1 at an earlier time/date.

The system S1 further includes a phantom model MF1 which also receives the resynchronization messages from the resynchronizer R1 of the system S1 and estimates state variables of the interface I1 from the resynchronization messages set by the resynchronizer R1 and received by the system S2. In other words, the phantom model MF1 produces an estimate based on the same data as that received by the remote model MD1 of the system S2. Thus the phantom model MF1 is used to model the variables of the interface I1 as modeled by the system S2.

The output of the phantom model MF1 is connected to the resynchronizer R1 which compares the estimate of the state variables from the phantom model MF1 and the state variables from the local model ML1. If the difference exceeds a predetermined threshold, the resynchronizer R1 sends a resynchronization message to the phantom model MF1 and to the extrapolator EXT1 of the system S2. Thus the volume of data exchanged between the systems S1 and S2 is relatively small because a resynchronization message is sent only if one of the two systems S1, S2 estimates that the other system S2, S1 is no longer able to estimate the variables correctly.

Figure 2:
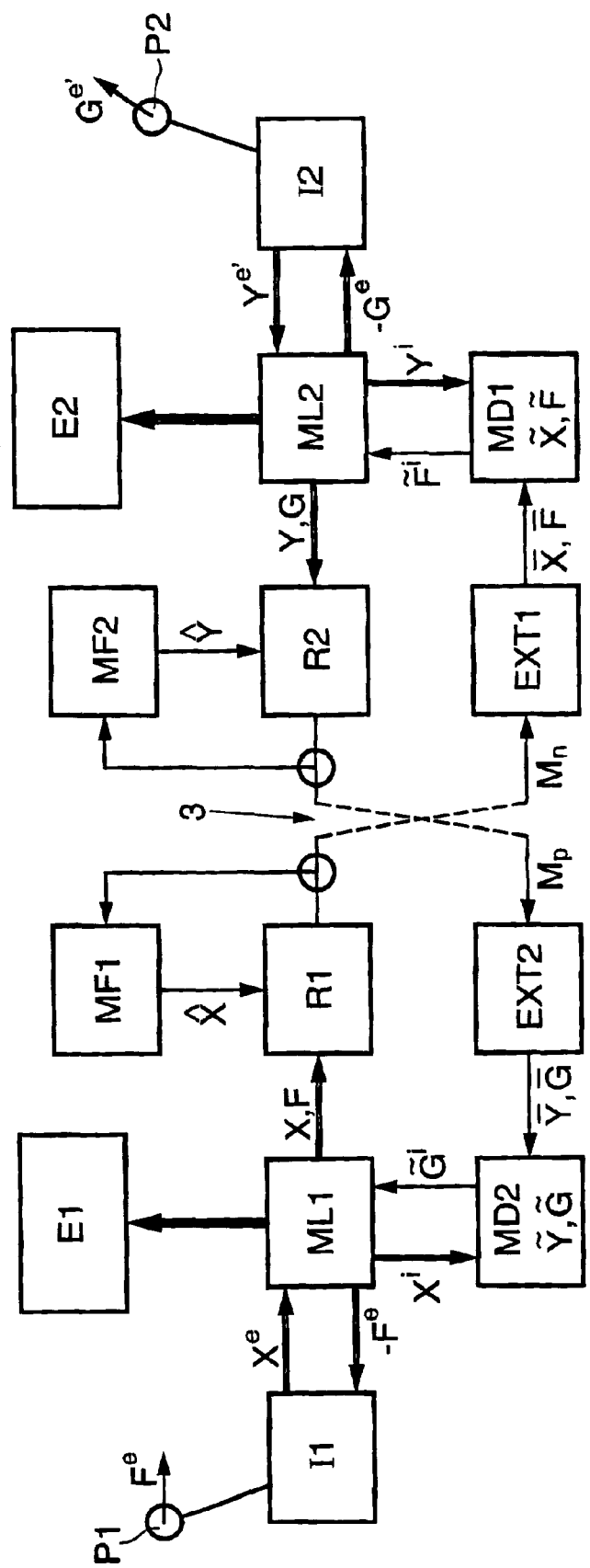
FIG. 2 shows a detail from FIG. 1.

How the system works is clear from FIG. 2. For the player J1, the state vector X breaks down into three parts: a variable part $X^e$ at the interface with the handgrip P1, a variable part $X^m$ internal to the mechanical model of the player J1, and an interaction variable $X^i$ at the interface with the other player. Similarly, the associated force or torque variable F breaks down into: a force $F^e$ exerted by the player J1 on the handgrip P1, a force $F^m$ exerted by gravity, other objects, or any other players, and the force $F^i$ exerted by the player J1 on the player J2. In a similar manner, the state vector Y of the player J2 breaks down into parts $Y^{ie}$, $Y^{im}$ and $Y^{ii}$ and the associated torque force vector G breaks down into parts $G^{ie}$, $G^{im}$ and $G^{ii}$. The two players J1 and J2 are in virtual contact. Thus $X^i = Y^i$. The law of action and reaction then yields: $F^i + G^{ii} = 0$.

On each time increment, the interface I1 captures the position $X^e_n$ and transmits it to the local model ML1. The interface I1 receives the set point force $F^e_n$ from the local model ML1 and uses the force feedback force $-F^e_n$ to control its actuator(s). Similarly, the interface I2 captures the position $Y^{ie}_n$ and transmits it to the local model ML2 and receives the force $G^{ie}_n$ from the local model ML2 and controls its actuator(s) with the force feedback force $-G^e_n$.

At the beginning of the time period n+1 the local model ML1 receives the position $X^e_{n+1}$ from the interface I1, the interaction estimate $\tilde{G}^i_{n+1}$ from the remote model MD2 and the prestored intrinsic variables $F^m_{n+1}$. The local model ML1 calculates the force exerted by the player J1 on the player J2:

$$F^i_{n+1} = \tilde{G}^i_{n+1}$$

and the force exerted by the player J1 on the handgrip P1:

$$F^e_{n+1} = B^{ee-1}\{X^e_{n+1} - X^e_n - A^e X_n - B^{em} F^m_{n+1} + B^{ei} \tilde{G}^i_{n+1}\},$$

the matrices A and B being those for the evolution of the player J1 with $X = AX + BF$. The local model ML1 then calculates:

$$X_{n+1}^{m,i} = X_n^{m,i} + A^{m,i}X_n + B^{m,i}\begin{bmatrix} F_{n+1}^e \\ F_{n+1}^m \\ -\tilde{G}_{n+1} \end{bmatrix}$$

The local model ML1 sends $X_{n+1}$ and $F_{n+1}$ to the resynchronizer R1, the set point $-F^e_{n+1}$ to the interface I1 and the position variable $X^i_{n+1}$ to the remote model MD2.

In the event that it does not receive a message from the resynchronizer R1, the phantom model MF1 calculates $\hat{F}_{n+1} = \hat{F}_n + K_1$, $K_1$ being provided by the system S2, and the position estimate $\hat{X}_{n+1} = (I+A)\hat{X}_n + B\hat{F}_{n+1}$, in other words the mechanical state of the player J1 such as it can be predicted by the system S2. Here I is the identity matrix.

When the phantom model MF1 receives a resynchronization message $M_n = \{n, \bar{X}_n, \bar{F}_n \text{ and } \bar{F}_{n-1}\}$ from the resynchronizer R1, it carries out the following resynchronization: $\hat{X}_n = \bar{X}_n$, $\hat{F}_n = \bar{F}_n$ and $K1 = \bar{F}_n - \bar{F}_{n-1}$.

In each time increment n the resynchronizer R1 receives the position variable $X_n$ and the force variable $F_n$ and $F_{n+1}$ from the local model ML1 and the estimate $\hat{X}_n$ from the phantom model MF1. It compares the absolute value of the difference between the position variable $X_n$ and the estimate $\hat{X}_n$ to a predetermined threshold and does nothing if said absolute value is below said threshold. If said absolute value is not below said threshold, it composes a resynchronization message $M_n = \{n, X_n, F_n, F_{n-1}\}$. The resynchronizer R1 sends the resynchronization message $M_n$ to the phantom model MF1 so that it resynchronizes itself immediately and to the remote model MD1 via the extrapolator EXT1 of the system S2 so that it resynchronizes itself as soon as possible.

The extrapolator EXT2 of the system S1 is used for synchronization. The message $M_p = \{p, Y_p, G_p, G_{p-1}\}$ sent by the resynchronizer R2 of the system S2 reaches the system S1 at a time from n to n+1. However, the message $M_p$ is stamped with the time/date p from the system S2. The extrapolator EXT2 calculates $K_2 = G_p - G_{p-1}$ and resynchronizes the remote model MD2 as follows: $\tilde{G}_p = G_p$ and $\tilde{Y}_p = Y_p$, and then at the subsequent times, and regardless of the outcome: $j = p, \ldots, n$, $\tilde{G}_{j+1} = \tilde{G}_j + K2$ and $\tilde{Y}_{j+1} = \tilde{Y}_j + C\tilde{Y}_j + D\tilde{G}_{j+1}$, C and D being the matrices equivalent to the matrices A and B for the player J2. The extrapolator EXT2 sends the remote model MD2 the resynchronization result $\tilde{Y}_{n+1}, \tilde{G}_{n+1}$ and $K_2$.

The remote model MD2 of the system S1 resynchronizes itself on receiving a message from the extrapolator EXT2, taking the values supplied by said extrapolator EXT2:

$\tilde{G}_{n+1} = \tilde{G}_{n+1}, \tilde{Y}_{n+1} = \tilde{Y}_{n+1}$ and $\tilde{K}_2 = K_2$ When not receiving any such message, and on each time increment, the remote model MD2 receives the position variable $X^i_{n+1}$ from the local model ML1 and performs a predictive calculation:

$\tilde{G}^{e',m'}_{n+1} = \tilde{G}^{e',m'}_n \tilde{K}^{e',m'}2$ $\tilde{G}^i_{n+1} = D^{ii-1}\{X^i_{n+1} - \tilde{Y}^i_n - C\tilde{Y}^i_n - D^{e'}G^{e'}_{n+1} - D^{m'}G^{m'}_{n+1}\}$ $\tilde{Y}^{e',m'}_{n+1} = \tilde{Y}^{e',m'}_n + C^{e',m'}\tilde{Y}_n + D^{e',m'}\tilde{G}_{n+1}$ $\tilde{Y}^i_{n+1} = X^i_{n+1}$ The remote model MD2 sends the local model ML1 the position variable prediction $\tilde{G}_{n+1}$ relating to the player J2.

The extrapolator EXT2 preferably effects a bevel resynchronization which smoothes the changes. One example of such resynchronization is shown in the FIG. 3 curves. Instead of changing the estimate of the position variable Y suddenly to the variable $\bar{Y}$ as calculated by the extrapolator EXT2 in the manner explained above, the resynchronization is effected in four steps between times n and n+4, as follows:

$k = |\tilde{Y}_{n+1} - \bar{Y}_{n+1}|/\text{threshold} + 1$.

If k=1, then $\tilde{Y}_{n+1} := \bar{Y}_{n+1}$.
If not, j=n, $\tilde{G}_{j+1} = \tilde{G}_j + K2$ $\bar{Y}_{j+1} = \bar{Y}_j + C\bar{Y}_j + D\tilde{G}_{j+1}$ $\tilde{Y}_{j+1} := \tilde{Y}_j + C\tilde{Y}_j + D\tilde{G}_{j+1}$ $\tilde{Y}_{j+1} = (\bar{Y}_{j+1} + (K-1)\tilde{Y}_{j+1})/k$ $j := j+1$ If k is greater than 2, then k:=k−1

Otherwise the loop is left and $\tilde{Y}_{j+1} = \bar{Y}_{j+1}$. The bevel resynchronization enables the system to operate more smoothly, which is better appreciated by users and entails fewer mechanical constraints.

More generally, the phantom model MF1 receives the same data as the remote model MD1 of the other system and can effect the same simulation as said other system. In other words, a search is conducted to find out what the other system does not know for the purposes of resynchronization. The resynchronizer works blind relative to the other system and enables simulation to continue in the absence of pertinent data transmitted by a resynchronization message from the other system. Especially in the case of bevel resynchronization, the extrapolator EXT2 takes account of movement as measured by the other system during the transmission time-delay caused by the communication network. In a simplified variant, it is perfectly conceivable for either or both systems to have no phantom model. A number of systems greater than two can equally be made to work together.

The local models represent the mechanical models of the two users. The remote models represent a remote replication of the local mechanical models which is necessarily approximate because of the time-delays on transmitting the states of the local models via the communication network. The phantom models represent an approximate local copy of the remote model. The remote models and the phantom models both work in predictor-corrector mode. The extrapolators extrapolate messages received with a certain time-delay to resynchronize the remote models to the clock value of the other system. The resynchronizers evaluate the necessity to launch a resynchronization message into the communication network as soon as there is too great a difference between the local models and the local witness predictive phantom models of the remote predictive models. The resynchronizers limit the number of messages sent via the communication network to avoid congestion on the network. Within a system, information can be exchanged at the rate of 1 kHz. Between the systems, and therefore via the communication network, messages are exchanged if one of the resynchronizers considers it to be necessary.

FIG. 4 shows an embodiment of the invention intended for ultrasound scanning. A control system S1 is installed in an establishment that does not specialize in obstetrics, for example in an establishment of a small town or in a vehicle serving rural areas. The system S2 is installed in a specialized hospital establishment in which highly qualified operators are available to perform the ultrasound scanning operations, for example a regional or teaching hospital. A patient J3 lies on a bed or a table T. An ultrasound scanning probe SE is in contact with their abdomen. A panel TR for adjusting parameters of the probe SE is installed nearby. The probe SE is connected to the system S1 and transmits ultrasound scanning image data to said system S1; it also exchanges data relating to the position of and to the actions exerted by the system S1. To clarify the drawing, the support of the probe SE is not shown; it can be an articulated arm. Nevertheless, it is to be understood that this support provides movement in space with several degrees of freedom, in general at least six degrees of freedom, so that a suitable position in contact with the abdomen of the patient J3 can be adopted. A microphone MI3 and a loudspeaker HP3 are connected to the system S1 to enable the patient to converse with the remote operator. A video camera CA3 points toward the patient J3 and a video screen EV3 enables the patient to see either the remote operator or the ultrasound scanning images. The video camera CA3 and the video screen EV3 are also connected to the system S1. In addition to the items described with reference to FIGS. 1 and 2, the systems S1 and S2 each include a multiplexer-demultiplexer DM1 and DM2 for transmitting data via the network 3, which can be an ADSL network, for example.

The operator J4 of the system S2, who can be a doctor specializing in ultrasound scanning, manipulates a handgrip P3 whose position in space is replicated by the probe SE. The handgrip P3 is connected to an articulated arm BA which is in turn connected to an interface I3 which is of the same kind as the interfaces I1 and I2 described above and includes one or more actuators and one or more position sensors and force sensors. The effect can be measured by measuring an actuator energy parameter, for example the current drawn, or by means of a strain gauge. The interface I3 is connected to the system S2.

A video camera CA4 points toward the operator J4 and the pictures it generates can be displayed on the screen EV3. A microphone MI4 and a loudspeaker HP4 enable the operator J4 to converse with the patient J3. These items are connected to the system S2. A large video screen EV4 displays a plurality of images simultaneously, for example an ultrasound scanning image, an image of the face of the patient J3 and an image showing the position of the probe SE on the abdomen of the patient.

What is claimed is:

1. A system for controlling the interaction of a first force feedback member with a second force feedback member, wherein the first force feedback member and the second force feedback member are communicably coupled, the system comprising:
    a local model, wherein the local model is configured to calculate a set point associated with the first force feedback member from:
        a variable measured by the first force feedback member,
        variables intrinsic to the first force feedback member; and
        an estimate of the interaction with the second member, and of a state variable of the first force feedback member;
    a remote model communicably coupled to the local model, wherein the remote model is configured to estimate the state variables of the second member and to receive updated data from the second member; and
    a resynchronizer communicably coupled to the local model wherein the resynchronizer is configured to send a resynchronization message to the second member.

2. The system of claim 1, further comprising a phantom model, wherein the phantom model is communicably coupled to the resynchronizer, wherein the phantom model is configured to estimate state variables of the first force feedback member based on resynchronization signals received from the resynchronizer.

3. The system of claim 2, wherein the resynchronizer comprises a comparator, wherein the comparator compares the estimate of the state variables from the phantom model with the state variables from the local model, wherein the resynchronizer is configured to send a resynchronization message to the phantom model and to the second force feedback member when the comparator determines that the difference between the state variables from the phantom model and the state variables from the local model exceeds a predetermined value.

4. The system of claim 1, further comprising an extrapolator, wherein the extrapolator is configured to receive a resynchronization message from the second force feedback member for updating the remote model of the first system.

5. A system for controlling a first force feedback member and a second remote force feedback member, wherein each member is provided with a control system, each of the control systems comprising:
    a local model, wherein the local model is configured to calculate a set point associated with the force feedback member from:
        a variable measured by the force feedback member,
        variables intrinsic to the force feedback member; and
        an estimate of the interaction with the other force feedback member and of a state variable of the force feedback member;
    a remote model communicably coupled to the local model, wherein the remote model is configured to estimate the state variables of the other force feedback member and to receive updated data from the other force feedback member; and
    a resynchronizer communicably coupled to the local model wherein the resynchronizer is configured to send a resynchronization message to the other force feedback member.

6. A method of controlling a force feedback member able to interact with a second force feedback member, the method comprising:
    using a local model to determine a set point associated with the first force feedback member from:
        a variable measured by the first force feedback member;
        variables intrinsic to the first force feedback member; and
        an estimate of the interaction with the second force feedback member and of a state variable of the first force feedback member;
    using a remote model to determine interactions and state variables of the second force feedback member;
    using a remote model to receive updating data from the second force feedback member; and
    generating a resynchronization message and sending it to the second force feedback member.

7. The method of claim 6, further comprising using a phantom model to estimate state variables of the first force feedback member based on resynchronization signals received from the resynchronizer.

8. The method of claim 7, wherein generating a resynchronization message comprises comparing the state variables from the phantom model with the state variables from the local model, wherein a resynchronization message is generated when the difference between the state variables from the phantom model and the state variables from the local model exceeds a predetermined value.

9. The method of claim 6, further comprising processing a resynchronization message from the second force feedback member with an extrapolator; and updating the remote model of the first force feedback member based on the received resynchronization message from the second force feedback member.

10. A computer program including program code for executing the steps of a method of controlling a first force feedback member able to interact with a second force feedback member when said program runs on a computer, the method comprising:

using a local model to determine a set point associated with the first force feedback member from:
a variable measured by the first force feedback member;
variables intrinsic to the first force feedback member; and
an estimate of the interaction with the second force feedback member and of a state variable of the first force feedback member;

using a remote model to determine interactions and state variables of the second force feedback member;

using a remote model to receive updating data from the second force feedback member; and generating a resynchronizatiOn message and sending it to the second force feedback member.

11. A medium capable of being read by a reader and storing program code means for executing the steps of a method of controlling a first force feedback member able to interact with a second force feedback member when the program runs on a computer, the method comprising:

using a local model to determine a set point associated with the first force feedback member from:
a variable measured by the first force feedback member;
variables intrinsic to the first force feedback member; and
an estimate of the interaction with the second force feedback member and of a state variable of the first force feedback member;

using a remote model to determine interactions and state variables of the second force feedback member;

using a remote model to receive updating data from the second force feedback member; and generating a resynchronization message and sending it to the second force feedback member.

* * * * *